US00PP10939P

United States Patent [19]

Zaiger et al.

[11] Patent Number: Plant 10,939

[45] Date of Patent: Jun. 1, 1999

[54] PEACH TREE 'JOANNA SWEET'

[76] Inventors: Chris Floyd Zaiger, 929 Grimes Ave.; Leith Marie Gardner, 1207 Grimes Ave.; Gary Neil Zaiger, 1907 Elm Ave.; Grant Gene Zaiger, 4005 California Ave., all of Modesto, Calif. 95358

[21] Appl. No.: 08/972,079

[22] Filed: Nov. 17, 1997

[51] Int. Cl.[6] ..... A01H 5/00

[52] U.S. Cl. ..... Plt./198

[58] Field of Search ..... Plt./43.2, 198, Plt./194, 197

*Primary Examiner*—Howard J. Locker
*Assistant Examiner*—Anne Marie Grünberg

[57] ABSTRACT

This new and unique variety of peach tree (*Prunus persica*) has the following desirable features that are outstanding in a new variety. The following features of the tree and its fruit are characterized with the tree budded on nemaguard rootstock, grown on Hanford sandy loam soil with Storie Index rating 95, in USDA hardiness zone 9, near Modesto, Calif., and with standard commercial cultural fruit growing practices, such as, pruning, thinning, spraying, irrigation, fertilization, etc.:

1. Heavy and regular production of large size fruit.
2. Fruit with a high degree of attractive red skin color.
3. Fruit with very firm flesh, good handling and shipping qualities.
4. Fruit with good, sweet, sub-acid flavor.
5. Fruit able to remain firm on the tree approximately 7 days past maturity (shipping ripe).
6. Vigorous, upright growth.

1 Drawing Sheet

ORIGIN OF THE VARIETY

This distinct variety of peach tree was originated by us in our experimental orchard located near Modesto, Calif., as a first generation cross between two selected seedlings with field identification numbers 55GA106 and 33EB323. The maternal parent (55GA106) originated as a first generation cross between O'Henry Peach (U.S. Plant Pat. No. 2,964) and 50G488. The selection 50G488 originated as a first generation cross of a seedling selection from seed of Early Sungrand Nectarine (U.S. Plant Pat. No. 1,420) crossed with Royal Gold Peach (U.S. Plant Pat. No. 2,663). The pollen parent (33EB323) originated as a selected seedling from open pollinated Sweet Gem Peach (U.S. Plant Pat. No. 7,952) seed. We grew and maintained a large group of these first generation seedlings under close observation and the present variety growing on its own root exhibited distinctive desirable characteristics of the tree and its fruit was selected for asexual reproduction and commercialization.

ASEXUAL REPRODUCTION OF THE VARIETY

Asexual reproduction of the new and distinct variety of peach tree was by budding to nemaguard rootstock, as performed by us in our experimental orchard located near Modesto, Calif., and shows that all characteristics of the tree and its fruit run true to the original tree and are established and transmitted through succeeding asexual propagations.

SUMMARY OF THE VARIETY

This new and distinct variety of peach tree is of large size, vigorous, upright growth; and is a regular and productive bearer of large, firm, yellow flesh freestone fruit. The fruit is further characterized by having excellent eating quality with good, sweet, sub-acid flavor. The fruit has an attractive red skin color, good handling and shipping qualities with the ability to remain firm on the tree approximately 7 days past maturity (shipping ripe). In comparison to Sweet Gem Peach (U.S. Plant Pat. No. 7,952), the fruit of the new variety is approximately 24 days later in maturity.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of peach tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:

*Size.*—Large — tree height pruned to 12 to 14 feet in height and 12 to 15 feet in width at maturity for economical harvesting of fruit.

*Vigor.*—Vigorous — tree growth during fruit growing season reaching 6 to 7 feet in height and 5 to 6 feet in width. During the first dormant season the tree is pruned to 3 to 4½ feet in height and 3 to 4 feet in width when selecting primary scaffolds and to promote proper tree growth for secondary scaffolds to be selected in second dormant season.

*Form.*—Usually pruned to vase shape.

*Productivity.*—Productive, fruit set is 2 or more times the amount desirable for normal crop load and fruit is thinned to desired number with proper spacing to develop desirable market size. Number of fruit set per tree varies with climatic conditions during bloom time.

*Bearer.*—Regular — number of fruit set each spring exceeds normal desirable crop load. Amount of thinning of fruit varies with number of trees per acre, soil type, climatic conditions and cultural practices.

*Density.*—Medium dense — light and air movement through tree is somewhat restricted with branches and leaves. Pruning to open the center of tree (vase shape) is desirable, giving more sunlight to enhance the fruit color, greater soluble solids (Brix), and keep fruit wood healthy.

*Growth.*—Upright.

Trunk:

*Size.*—Large.

*Texture.*—Medium shaggy.

*Color.*—Brown to soot brown (5-E-4) to (5-F-5).

Branches:

*Size.*—Medium.

*Texture.*—Smooth to medium rough.

*Lenticels.*—Medium number. Medium to large size.

*Color.*—Light brown to brown (5-D-6) to (5-E-6). Varies with age of growth.

Leaves:

*Size.*—Large. Average length 6". Average width 1⅜".

*Form.*—Lanceolate.

*Margin.*—Crenate.

*Thickness.*—Medium.

*Surface.*—Smooth.

*Petiole.*—Medium length. Medium thickness.

*Glands.*—Globose. Number varies from 0 to 4. Average number 2. Located on lower portion of leaf blade and upper portion of petiole.

*Color.*—Upper surface — green to deep green (27-E-5) to (27-F-8). Lower surface — light green to green (27-E-4) to (27-E-6).

Flower buds:

*Size.*—Large.

*Length.*—Long.

*Forms.*—Plump.

*Pubescence.*—Pubescent.

Flowers:

*Size.*—Large, showy. 1¼" to 1½" in diameter.

*Pollen.*—Present, self fertile.

*Blooming period.*—Date of first bloom: Mar. 5, 1996. Date of full bloom: Mar. 9, 1996. Varies slightly with climatic conditions.

*Color.*—Pink to light pink (10-A-3) to (10-A-2). Color fades with age of bloom.

Fruit:

*Maturity when described.*—Firm ripe.

*Date of first picking.*—Jul. 3, 1996.

*Date of last picking.*—Jul. 10, 1996. Varies slightly with climatic conditions.

*Size.*—Large. Average diameter axially 2¾". Average transversely in suture plane 3". Average weight 188 grams, varies from 180 to 202 grams.

*Forms.*—Nearly globose, slightly flattened at stem end. Some fruit with slight apical point.

*Suture.*—Shallow, extends from base to apex.

*Ventral surface.*—Usually rounded, some fruit very slightly lipped.

*Apex.*—Usually rounded, varies from slight pistil point to slight depression.

*Base.*—Retuse.

*Cavity.*—Rounded to slightly elongated in suture plane. Average depth ½". Average breadth ¾".

Flesh:

*Ripens.*—Evenly.

*Texture.*—Firm.

*Fibers.*—Few, tender.

*Aroma.*—Moderate.

*Amygdalin.*—Undetected.

*Eating quality.*—Excellent.

*Flavor.*—Good, sub-acid, sweet.

*Juice.*—Moderate amount, average Brix 12.1°, sweet, enhances flavor.

*Color.*—Varies from pastel yellow to yellow (3-A-4) to (3-A-7). Pit cavity — yellowish gray to grayish yellow (4-B-4) to (4-C-4), with slight amount of red to strawberry red (10-D-6) to (10-D-8).

Stem:

*Size.*—Length varies from 7/32" to ¼". Diameter ⅛". Enlarged at point of fruit attachment.

Skin:

*Thickness.*—Medium.

*Texture.*—Medium, tenacious to flesh.

*Down.*—Moderate amount. Short in length.

*Tendency to crack.*—Slight.

*Color.*—Pastel yellow to yellow ground color (3-A-4) to (3-A-6). Overspread with red to strawberry red (10-D-6) to (10-D-8). Fruit expose to direct sunlight have greater enhancement of red color than fruit shaded with little or no direct sunlight, amount of enhanced red color varies with weather conditions during maturity time.

Stone:

*Type.*—Freestone.

*Size.*—Large. Average length 1½". Average width 1". Average thickness ¾".

*Form.*—Ovoid.

*Base.*—Varies from rounded to straight.

*Apex.*—Usually acuminate, varies from acuminate to rounded.

*Surface.*—Irregularly furrowed toward apex, pitted throughout, heavier toward base. Pits vary from round to elongated.

*Sides.*—Equal to unequal. Some stones have one side slightly larger, extending farther from suture plane and having slightly deeper and larger furrows and pits.

*Tendency to split.*—None.

*Color.*—Brown to reddish brown (8-C-6) to (8-D-6).

Use: Dessert. Market, local and long distance.

Keeping quality: Good — held well in cold storage for 10 days and maintained good firmness and eating quality.

Shipping quality: Good — minimal bruising or scarring in packing and shipping trials.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of peach tree, substantially as illustrated and described, characterized by its large size, vigorous upright growth; and by being a regular and productive bearer of large, firm, freestone fruit with a high degree of attractive red skin color; the fruit is further characterized as having good handling and shipping qualities, good, sweet, sub-acid flavor, and in comparison to Sweet Gem Peach (U.S. Plant Pat. No. 7,952), the fruit matures approximately 24 days later.

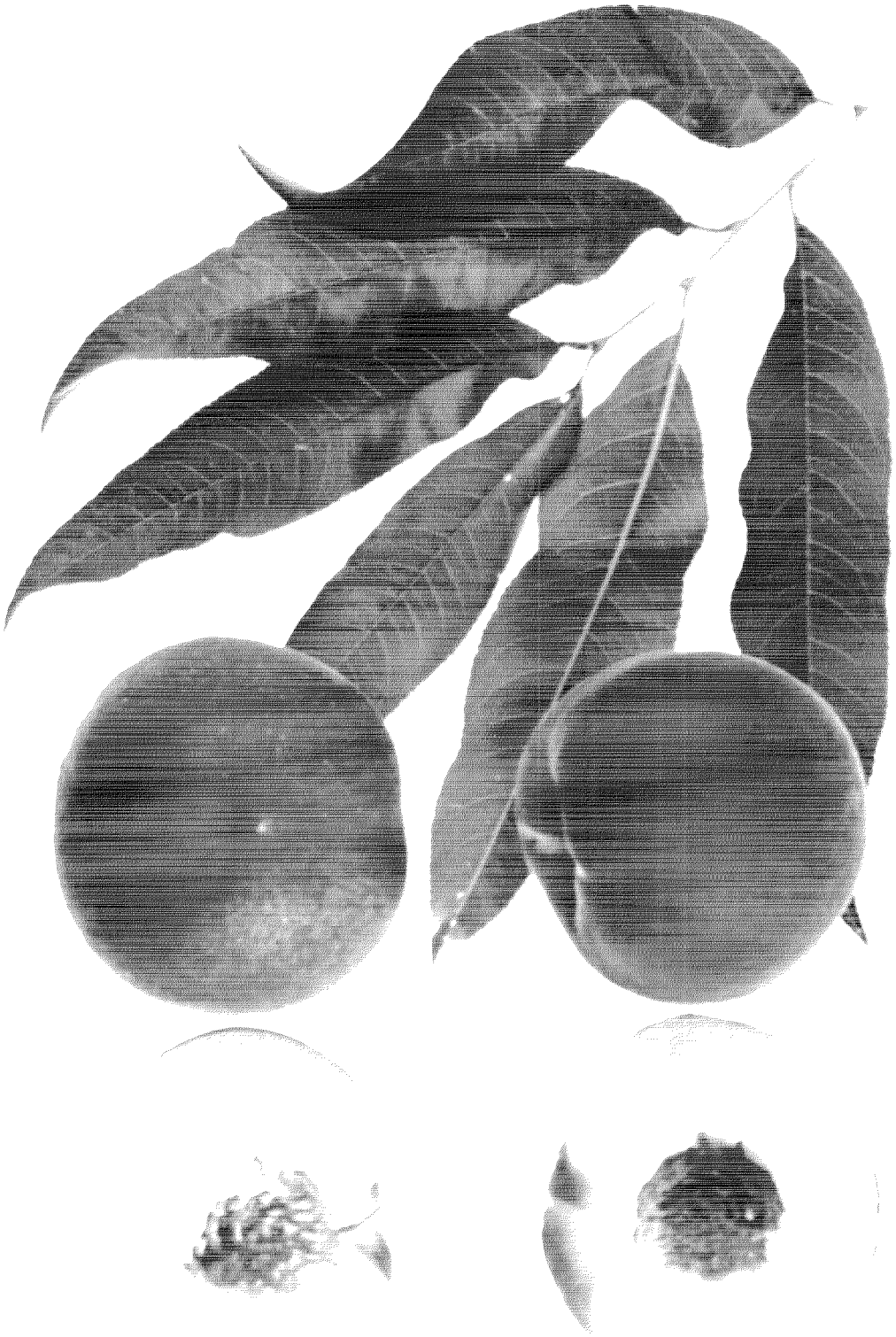

* * * * *